(12) United States Patent
DoBrava et al.

(10) Patent No.: US 6,974,468 B2
(45) Date of Patent: Dec. 13, 2005

(54) FILTER RETRIEVAL CATHETER

(75) Inventors: Eric M. DoBrava, Crystal, MN (US); Jeffrey H. Vogel, Brooklyn Park, MN (US); Brian J. Lowe, Fridley, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 345 days.

(21) Appl. No.: 09/795,833

(22) Filed: Feb. 28, 2001

(65) Prior Publication Data

US 2002/0120286 A1 Aug. 29, 2002

(51) Int. Cl.$^7$ .............................................. A61M 29/00
(52) U.S. Cl. ....................... 606/200; 606/108; 606/198; 604/96.01; 604/264
(58) Field of Search ................................ 606/200, 108, 606/198, 191; 604/96.01, 264

(56) References Cited

U.S. PATENT DOCUMENTS

| | | | |
|---|---|---|---|
| 5,792,157 A | 8/1998 | Mische et al. | |
| 5,980,555 A | 11/1999 | Barbut et al. | |
| 6,042,598 A | 3/2000 | Tsugita et al. | |
| 6,051,015 A | 4/2000 | Maahs | |
| 6,066,149 A | 5/2000 | Samson et al. | |
| 6,066,158 A | 5/2000 | Engelson et al. | |
| 6,117,154 A | 9/2000 | Barbut et al. | |
| 6,136,016 A | 10/2000 | Barbut et al. | |
| 6,171,328 B1 | 1/2001 | Addis | |
| 6,206,868 B1 | 3/2001 | Parodi | |
| 6,221,006 B1 | 4/2001 | Dubrul et al. | |
| 6,224,620 B1 | 5/2001 | Maahs | |
| 6,231,544 B1 | 5/2001 | Tsugita et al. | |
| 6,235,044 B1 | 5/2001 | Root et al. | |
| 6,235,045 B1 | 5/2001 | Barbut et al. | |
| 6,238,412 B1 | 5/2001 | Dubrul et al. | |
| 6,245,087 B1 | 6/2001 | Addis | |

(Continued)

FOREIGN PATENT DOCUMENTS

| | | |
|---|---|---|
| DE | 199 16 162 | 10/2000 |
| EP | 1 127 556 A2 | 8/2001 |
| FR | 2 694 687 | 8/1992 |
| WO | WO 00/07521 | 2/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |

(Continued)

*Primary Examiner*—Henry Bennett
*Assistant Examiner*—Andrea M. Ragonese
(74) *Attorney, Agent, or Firm*—Crompton Seager & Tufte LLC

(57) ABSTRACT

Methods and devices for retrieving a filter fixed to a guidewire disposed within a blood vessel are disclosed. A catheter for retrieving a filter fixed to a guidewire disposed within a blood vessel in accordance with the present invention includes an elongate shaft and a housing fixed to the elongate shaft proximate a distal end thereof. A tip member is slidingly disposed within a cavity defined by the housing. In a preferred embodiment, the tip member is configured such that the housing is substantially centered about the guidewire. In another preferred embodiment, the tip member is slidingly disposed within the housing, and the tip member may be moved between a first position and a second position.

40 Claims, 6 Drawing Sheets

U.S. PATENT DOCUMENTS

| | | |
|---|---|---|
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer et al. |
| 6,309,399 B1 | 10/2001 | Barbut et al. |
| 6,319,268 B1 | 11/2001 | Ambrisco et al. |
| 6,344,049 B1 | 2/2002 | Levinson et al. |

FOREIGN PATENT DOCUMENTS

| | | |
|---|---|---|
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01/67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |

FILTER RETRIEVAL CATHETER

FIELD OF THE INVENTION

The present invention relates generally to devices and methods for treating occluded or stenoic blood vessels. More particularly, the present invention relates to devices and methods for removing a filter which has been placed in a blood vessel during a procedure to remove an occlusion or stenosis.

BACKGROUND OF THE INVENTION

It is critical that the heart muscle be well oxygenated so that the blood pumping action of the heart is not impaired. Blood vessels which have become occluded (blocked) or stenotic (narrowed) may interrupt the oxygen supply to the heart muscle.

Occluded or stenotic blood vessels may be treated with a number of medical procedures including angioplasty and atherectomy. Angioplasty techniques such as percutaneous transluminal angioplasty (PTA) and percutaneous transluminal coronary angioplasty (PTCA) are relatively non-invasive methods of treating a stenotic lesion. These angioplasty techniques typically involve the use of a guidewire and a balloon catheter. In these procedures, a balloon catheter is advanced over a guidewire such that the balloon is positioned proximate a restriction in a diseased vessel. The balloon is then inflated and the restriction in the vessel is opened. During an atherectomy procedure, the stenotic lesion is mechanically cut or abraded away from the blood vessel wall using an atherectomy catheter.

During atherectomy procedures, stenotic debris that is separated from the stenosis may be free to flow within the lumen of the vessel. If this debris enters the circulatory system, it may facilitate the formation of an occlusion in the neural vasculaturre, or in the lungs, both of which are highly undesirable. An occlusion in the neural vasculatture may cause a stroke, and an occlusion in the lungs may interfere with the oxygenation of the blood. During angioplasty procedures, stenotic debris may also break loose due to manipulation of the blood vessel.

SUMMARY OF THE INVENTION

The present invention relates generally to devices and methods for treating occluded or stenoic blood vessels. More particularly, the present invention relates to devices and methods for removing a filter which has been placed in a blood vessel during a procedure to remove an occlusion or stenosis. A filter retrieval catheter in accordance with an exemplary embodiment of the present invention includes an elongate shaft defining a lumen. A shaft hub is disposed about the elongate shaft proximate a proximal end thereof. A filter housing is fixed to the elongate shaft proximate a distal end thereof. The filter housing preferably has a proximal portion and a distal portion. A tip member is preferably slidingly disposed within the distal portion of the filter housing.

The tip member of the filter retrieval catheter preferably has an extended position and a retracted position. The filter retrieval catheter preferably includes a distal stop mechanism that is adapted to stop the movement of the tip member to the filter housing when the tip member is in the extended position. When the tip member is in the extended position, a tapered distal portion of the tip member preferably extends distally from the filter housing. The tapered distal portion of the tip member preferably has a generally conical shape. The generally conical shape of the tapered distal portion may facilitate the tracking of the filter retrieval catheter as it is advanced through a blood vessel.

The filter retrieval catheter preferably also includes a proximal stop mechanism that is adapted to stop relative movement between the tip member and the filter housing when the tip member is in the retracted position. In one embodiment, the proximal stop mechanism includes a trailing surface of the tip member and a mating surface defined a portion of the filter housing. In this embodiment, the trailing surface of the tip member seats against the mating surface when the tip member is in the retracted position. In a particularly preferred embodiment, the proximal stop mechanism is adapted to provide a hard stop that may be sensed by a physician using the filter retrieval catheter in a surgical procedure. This hard stop provides tactile feedback indicating that the tip member has been successfully placed in the retracted position.

In a preferred embodiment, the filter retrieval catheter includes a guidewire lumen extending through the tip member. In a preferred embodiment, the tip member is configured such that guidewire is substantially centered within the filter housing. Centering the filter housing about guidewire may facilitate the tracking of the filter retrieval catheter as it is advanced along a guidewire disposed within a blood vessel. Centering the filter housing may also reduce the magnitude of force which is required to urge the filter housing over a filter or other collapsible device attached to guidewire.

In one embodiment, the filter housing has an inner diameter and the tip member has an outer radial extent comprising an outer diameter. In a preferred embodiment, the outer diameter of the tip member is similar to the inner diameter of the filter housing. In a particularly preferred embodiment, the outer diameter of the tip member is slightly smaller than inner diameter of the filter housing.

In one embodiment, an inner tubular member extends proximally from the tip member. The inner tubular member preferably has an outer radial extent which is generally smaller than the outer radial extent of the tip member. In one embodiment, the inner tubular member extends through a shaft lumen defined by the elongate shaft. The elongate shaft is preferably slidingly disposed about the inner tubular member. A shaft hub is disposed about the elongate shaft proximate a proximal end thereof. An ancillary hub is disposed about the inner tubular member proximate the proximal end thereof. The inner tubular member preferably enables a physician to remotely move the tip member between the extended position and the retracted position.

The filter retrieval catheter may be utilized to remove a filter from a blood vessel. In a preferred embodiment, the physician may manipulate the distal portion of the filter retrieval catheter by applying forces to the proximal portion of the filter retrieval catheter. In a particularly preferred embodiment, the filter retrieval catheter is adapted to provide hard stops that may be sensed by a physician using the filter retrieval catheter in a surgical procedure. These hard stops provide tactile feedback indicating that the tip member has been successfully placed in the desired position. Also in a preferred embodiment, the filter is urged into a contracted configuration when it is disposed within the filter housing and is free to assume an expanded configuration when it is outside of the filter housing.

DETAILED DESCRIPTION OF THE INVENTION

The following detailed description should be read with reference to the drawings, in which like elements in different drawings are numbered in like fashion. The drawings which are not necessarily to scale, depict selected embodiments and are not intended to limit the scope of the invention. In some cases, the drawings may be highly diagrammatic in nature. Examples of constructions, materials, dimensions, and manufacturing processes are provided for various elements. Those skilled in the art will recognize that many of the examples provided have suitable alternatives that may be utilized.

Figure 1:
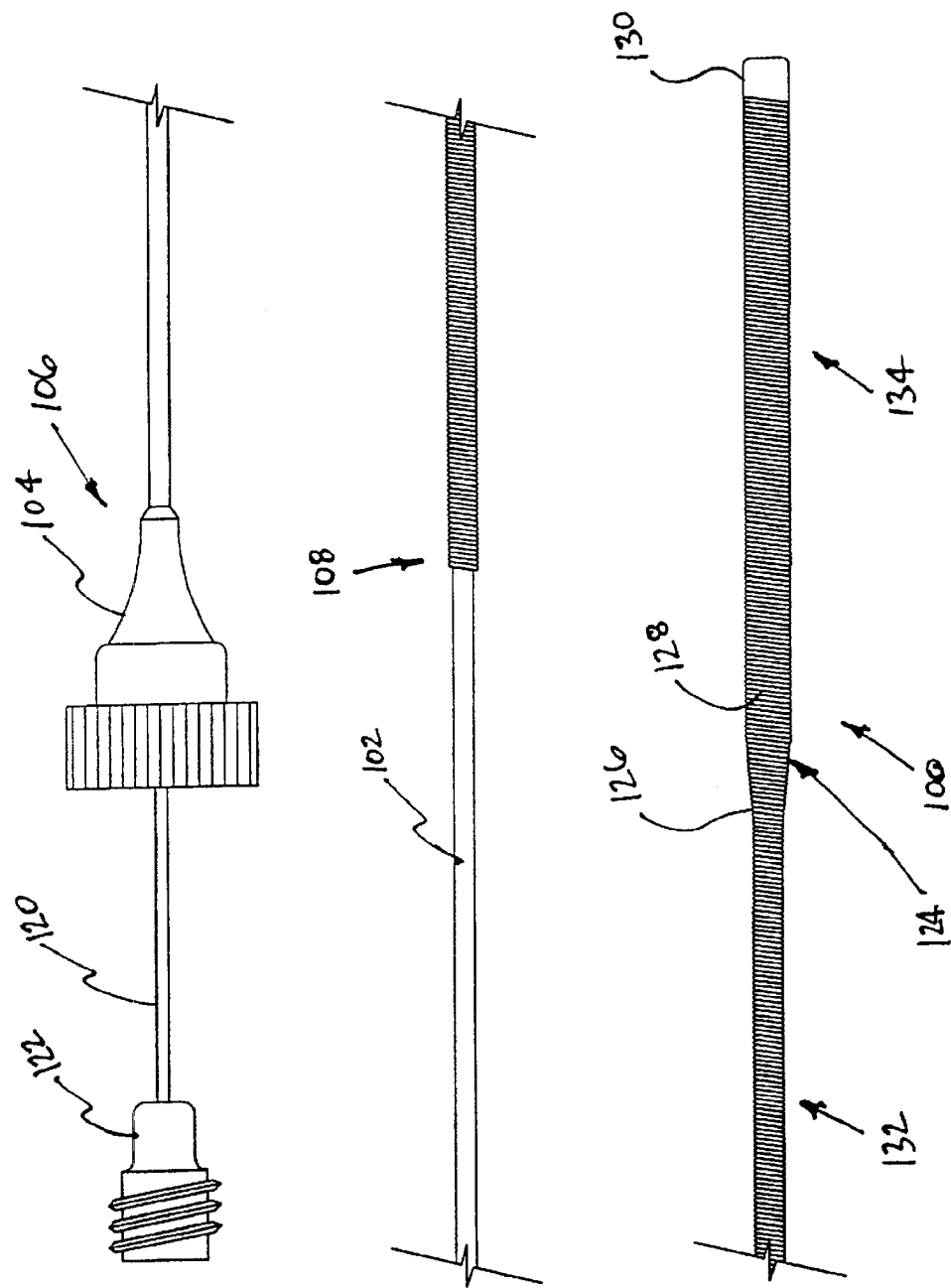
FIG. 1 is a plan view of a filter retrieval catheter in accordance with an exemplary embodiment of the present invention.

FIG. 1 is a plan view of a filter retrieval catheter 100 in accordance with an exemplary embodiment of the present invention. Filter retrieval catheter 100 comprises an elongate shaft 102 defining a lumen. A shaft hub 104 is disposed about elongate shaft 102 proximate a proximal end 106 thereof.

In FIG. 1, an inner tubular member 120 can be seen extending proximally from proximal end 106 of elongate shaft 102. Inner tubular member 120 is, preferably, slidingly disposed within the lumen defined by elongate shaft 102. An ancillary hub 122 is disposed about inner tubular member 120 proximate the proximal end thereof.

Filter retrieval catheter 100 includes a filter housing 124 that is fixed to elongate shaft 102 proximate a distal end 108 thereof. In the embodiment of FIG. 1, filter housing 124 comprises a wire 126 forming a plurality of turns 128. In a preferred embodiment, adjacent turns 128 are disposed in close proximity to one another. In a particularly preferred embodiment, adjacent turns 128 contact each other across substantially their entire length. In this particularly preferred embodiment, filter housing 124 has a high level of longitudinal pushability and a high level of lateral flexibility. In the embodiment of FIG. 1, filter housing 124 includes an a traumatic tip 130 that is fixed to the distal end thereof.

The term "wire", as used in describing wire 126 should not be mistaken as limiting wire 126 to elements having a circular cross section. The cross section of wire 126 may be any number of shapes. For example, the cross section of wire 126 could be rectangular, elliptical, etc. Likewise, the term "wire", as used in describing wire 126 should not be mistaken as being limited to metallic materials. In fact, wire 126 may be comprised of many metallic and non-metallic materials. Examples of metallic materials that may be suitable in some applications include stainless steel, tantalum, gold, and titanium. Wire 126 may also include a nickel-titanium alloy known in the art as Nitinol. Nitinol is commercially available from Memry Technologies (Brookfield, Conn.), TiNi Alloy Company (San Leandro, Calif.), and Shape Memory Applications (Sunnyvale, Calif.). Examples of non-metallic materials that may be suitable in some applications may be found in the list immediately below which is not exhaustive: polycarbonate, poly(L-lactide) (PLLA), poly(D,L-lactide) (PLA), polyglycolide (PGA), poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), polyD,L-lactide-co-caprolactone) (PLA/PCL), poly(glycolide-co-caprolactone) (PGA/PCL), polyanhydrides (PAN), poly(ortho esters), poly (phoshate ester), poly(amino acid), poly(hydroxy butyrate), polyacrylate, polyacrylamid, poly(hydroxyethyl methacrylate), polyurethane, polysiloxane and their copolymers. Embodiments of the present invention have also been envisioned in which wire 126 has a tubular cross section.

Filter housing 124 has a proximal portion 132 and a distal portion 134. In a preferred embodiment, inner tubular member 120 extends distally into distal portion 134 of filter housing 124. Also in a preferred embodiment, a tip member 136 is disposed about inner tubular member 120 proximate it's distal end. In the embodiment of FIG. 1, tip member 136 is entirely disposed within filter housing 124. A portion of tip member 136 is visible in FIG. 2.

Figure 2:
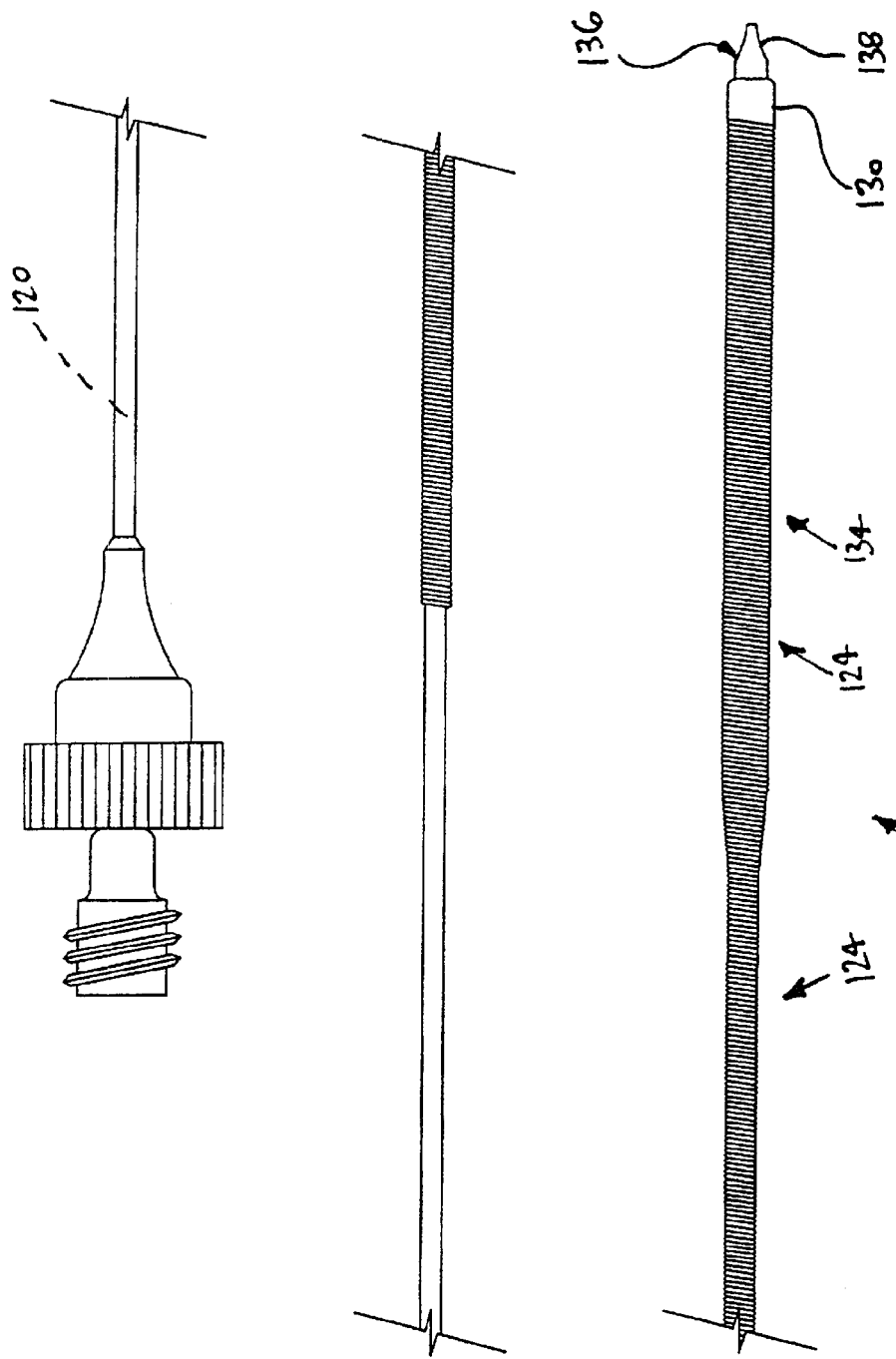
FIG. 2 is an additional plan view of filter retrieval catheter of FIG. 1.

FIG. 2 is an additional plan view of filter retrieval catheter 100 of FIG. 1. In the embodiment of FIG. 2, inner tubular member 120 has been advanced distally so that tip member 136 extends distally from filter housing 124. In the embodiment of FIG. 1 and FIG. 2, distal portion 134 of filter housing 124 is enlarged relative to proximal portion 132. In a preferred embodiment, distal portion 134 is adapted to slidingly receive tip member 136. Tip member 136 includes a tapered distal portion 138. The generally conical shape of tapered distal portion 138 may facilitate the tracking of filter retrieval catheter 100 as it is advanced through a blood vessel.

Filter housing 124 preferably includes an atraumatic tip 130 that is fixed to wire 126. Atraumatic tip 130 preferably defines a tip lumen that is adapted to accept tip member 136. In the embodiment of FIG. 2, tip member 136 extends through the tip lumen such that atraumatic tip 130 is disposed about tip member 136.

Figure 3:
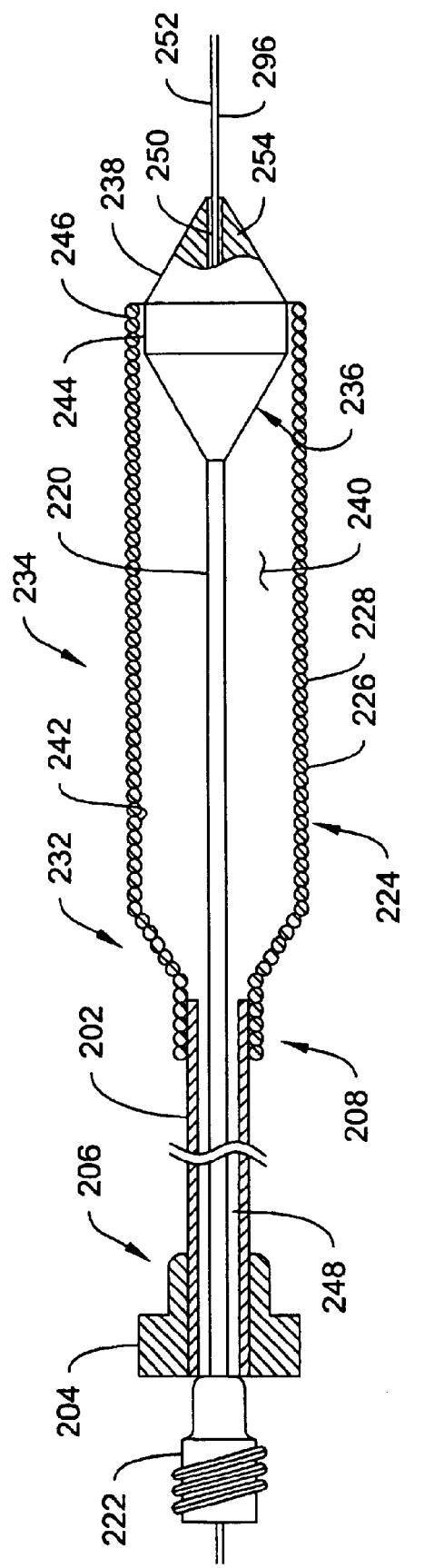
FIG. 3 is a partial cross-sectional view of a filter retrieval catheter in accordance with an additional exemplary embodiment of the present invention.

FIG. 3 is a partial cross-sectional view of a filter retrieval catheter 200 in accordance with an additional exemplary embodiment of the present invention. In FIG. 3, a guidewire 296 is seen extending through a guidewire lumen of filter retrieval catheter 200. Filter retrieval catheter 200 includes a filter housing 224 fixed to an elongate shaft 202 proximate a distal end 208 thereof. Filter housing 224 has a proximal portion 232 and a distal portion 234.

A tip member 236 of filter retrieval catheter 200 is partially disposed within a housing lumen 240 defined by distal portion 234 of filter housing 224. The position of tip member 236 shown in FIG. 3 may be referred to as an extended position. When tip member 236 is in the extended position, a tapered distal portion 238 of tip member 236 preferably extends distally from filter housing 224. The generally conical shape of tapered distal portion 238 may facilitate the tracking of filter retrieval catheter 200 as it is advanced through a blood vessel. Tip member 236 of filter retrieval catheter 200 preferably also has a retracted position. Filter housing 224 and tip member 236 are preferably configured such that filter housing 224 may accept a filter when tip member 236 is in the retracted position.

In a preferred embodiment, tip member 236 is configured such that guidewire 226 is substantially centered within filter housing 224. Centering filter housing 224 about guidewire 226 may facilitate the tracking of filter retrieval catheter 200 as it is advanced along a guidewire disposed within a blood vessel. Centering filter housing 224 about guidewire 226 may also reduce the magnitude of force which is required to urge filter housing 224 over a filter or other collapsible device attached to guidewire 226.

Distal portion 234 of filter housing 224 has an inner diameter 242. Tip member 236 has an outer radial extent 244 comprising an outer diameter 246. In a preferred embodiment, outer diameter 246 of tip member 236 is similar to inner diameter 242 of filter housing 224. In a particularly preferred embodiment, outer diameter 246 of tip member 236 is slightly smaller than inner diameter 242 of filter housing 224.

An inner tubular member 220 extends proximally from tip member 236. Inner tubular member preferably has an outer radial extent that is generally smaller than outer radial extent 244 of tip member 236. In the embodiment of FIG. 3, inner tubular member 220 extends through a shaft lumen 248 defined by elongate shaft 202. Elongate shaft 202 is preferably slidingly disposed about inner tubular member 220. A shaft hub 204 is disposed about elongate shaft 202 proximate a proximal end 206 thereof. An ancillary hub 222 is disposed about inner tubular member 220 proximate the proximal end thereof.

In a preferred embodiment, filter retrieval catheter 200 includes a guidewire lumen 250 extending through tip member 236, inner tubular member 220, and ancillary hub 222. In FIG. 3, guidewire 296 is partially disposed within guidewire lumen 250. Guidewire 296 has a guidewire diameter 252 and Guidewire lumen 250 has a guidewire lumen diameter 254. In a preferred embodiment, guidewire lumen diameter 254 is similar to guidewire diameter 252. In a particularly preferred embodiment, guidewire lumen diameter 254 is slightly larger than guidewire diameter 252.

In the embodiment of FIG. 3, filter housing 224 comprises a wire 226 forming a plurality of turns 228. In a preferred embodiment, adjacent turns 228 are disposed in close proximity to one another. In a particularly preferred embodiment, adjacent turns 228 contact each other across substantially their entire length. In this particularly preferred embodiment, filter housing 224 has a high level of longitudinal pushability and a high level of lateral flexibility. The term "wire", as used in describing wire 226 should not be mistaken as limiting wire 226 to elements having a circular cross section. The cross section of wire 226 may be any number of shapes. For example, the cross section of wire 226 could be rectangular, elliptical, etc. Likewise, the term "wire", as used in describing wire 226 should not be mistaken as being limited to metallic materials. In fact, wire 226 may be comprised of many metallic and non-metallic materials.

Figure 4:
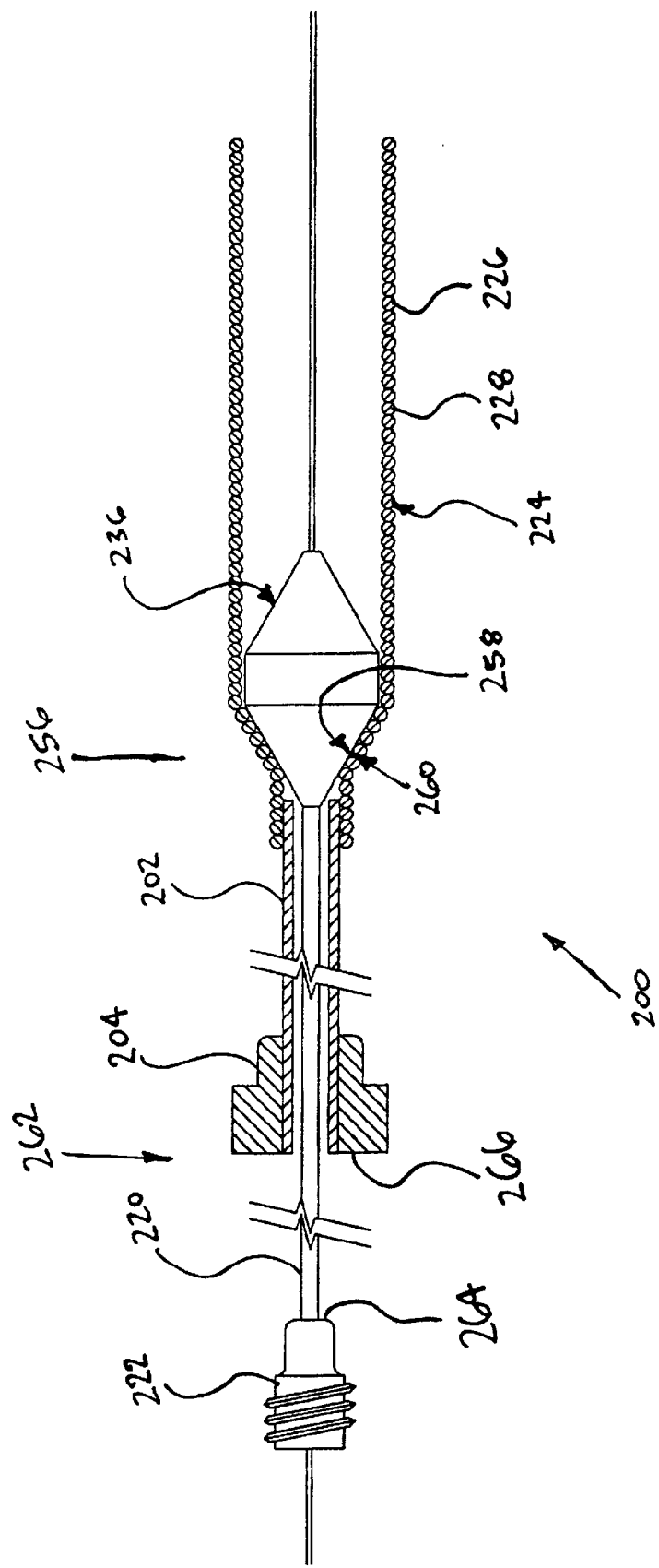
FIG. 4 is an additional partial cross-sectional view of filter retrieval catheter of FIG. 3.

FIG. 4 is an additional partial cross-sectional view of filter retrieval catheter 200 of FIG. 3. In the embodiment of FIG. 4, inner tubular member 220 has been moved relative to elongate shaft 202 so that tip member 236 is disposed in the retracted position.

Filter retrieval catheter 200 preferably includes a proximal stop mechanism 256 that is adapted to stop relative movement between tip member 236 and filter housing 224 when tip member 236 is in the retracted position. In the embodiment of FIG. 4, proximal stop mechanism 256 includes a trailing surface 258 of tip member 236 and a mating surface 260 defined by a plurality of turns 228 of wire 226 of filter housing 224. In the embodiment of FIG. 4, trailing surface 258 of tip member 236 seats against mating surface 260 when tip member 236 is in the retracted position. In a particularly preferred embodiment, proximal stop mechanism 256 is adapted to provide a hard stop that may be sensed by a physician using filter retrieval catheter 200 in a surgical procedure. This hard stop provides tactile feedback indicating that tip member 236 has been successfully placed in the retracted position.

As mentioned previously, tip member 236 of filter retrieval catheter 200 preferably has both a retracted position as shown in FIG. 4 and an extended position as shown in FIG. 3. Filter retrieval catheter 200 preferably includes a distal stop mechanism 262 that is adapted to stop the movement of tip member 236 and inner tubular member 220 relative to filter housing 224 when tip member 236 is in the extended position.

In the embodiment of FIG. 4, distal stop mechanism 262 includes a distal surface 264 of ancillary hub 222 and a proximal surface 266 of shaft hub 204. In the embodiment of FIG. 4, distal surface 264 of ancillary hub 222 may seat against proximal surface 266 of shaft hub 204 when tip member 236 is placed in the extended position.

Figure 5:
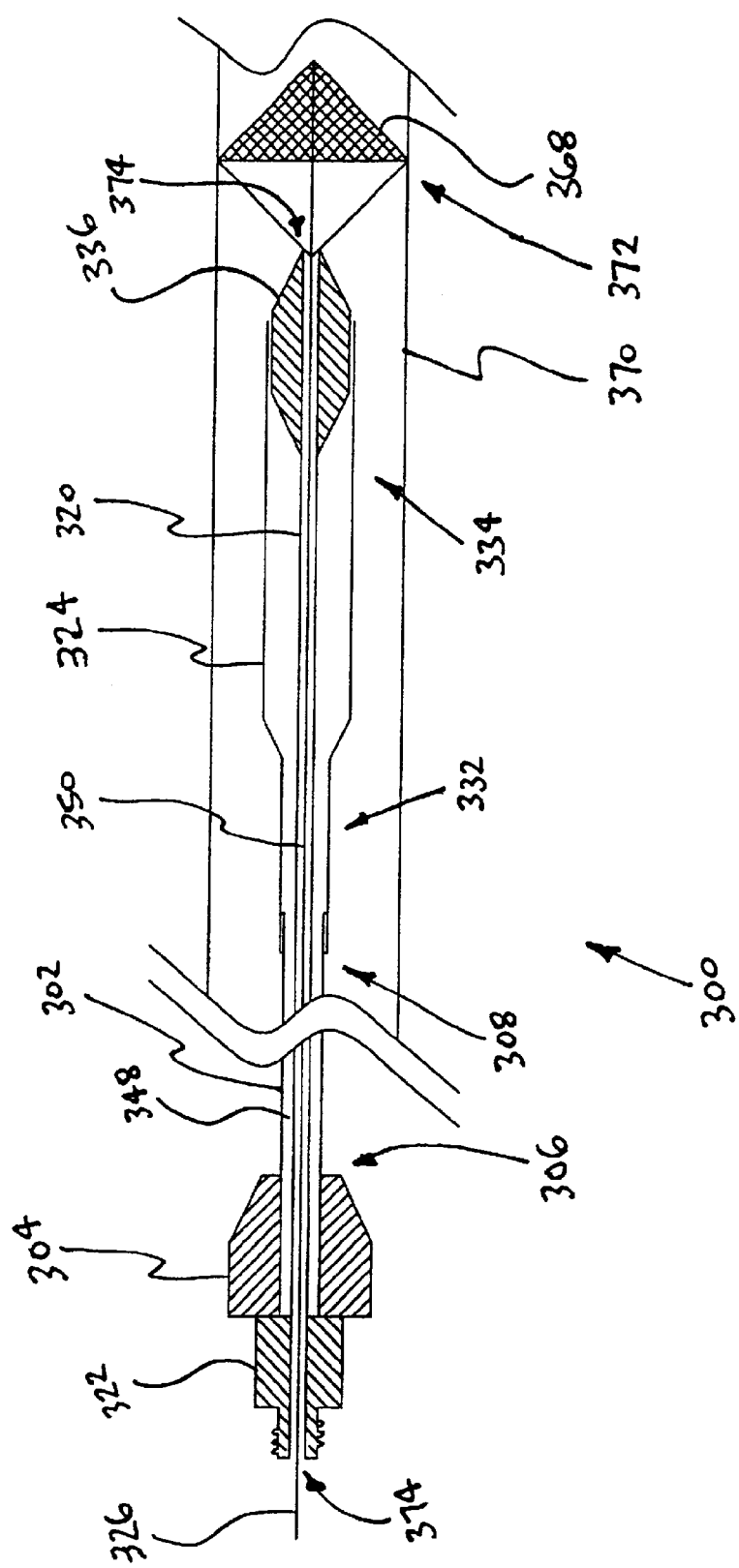
FIG. 5 is a partial cross-sectional view of a filter retrieval catheter in accordance with yet another exemplary embodiment of the present invention.

FIG. 5 is a partial cross-sectional view of a filter retrieval catheter 300 in accordance with yet another exemplary embodiment of the present invention. Filter retrieval catheter 300 may be utilized to retrieve a filter 368 that was previously delivered to a target location 372 in a blood vessel 370. In the embodiment of FIG. 5, a distal portion of filter retrieval catheter 300 is disposed within blood vessel 370 such that a tip member 336 of filter retrieval catheter 300 is disposed proximate filter 368. Filter retrieval catheter 300 preferably extends out of blood vessel 370, and a proximal portion of filter retrieval catheter 300 is preferably disposed outside of the patient's body so that it is easily accessible to a physician.

Tip member 336 of filter retrieval catheter 300 is preferably fixed to an inner tubular member 320 of filter retrieval catheter 300 proximate a distal end thereof. Inner tubular member 320 of filter retrieval catheter 300 is, preferably, slidingly disposed within a shaft lumen 348 defined by an elongate shaft 302 of filter retrieval catheter 300. An ancillary hub 322 is disposed about inner tubular member 320 proximate a proximal end thereof. In FIG. 5, it may be appreciated that a guidewire lumen 350 extends through ancillary hub 322, inner tubular member 320, and tip member 336. Ancillary hub 322 defines a proximal guidewire port 374 in fluid communication with guidewire lumen 350. Tip member 336 defines a proximal guidewire port 374 in fluid communication with guidewire lumen 350.

Filter retrieval catheter 300 includes an elongate shaft 302. In FIG. 5, it may be appreciated that tip member 336 is disposed within a filter housing 324 that is fixed to elongate shaft 302 proximate a distal end 308 thereof. A shaft hub 304 is disposed about elongate shaft proximate a proximal end 306 thereof.

Filter housing 324 has a proximal portion 332 and a distal portion 334. In the embodiment of FIG. 5, distal portion 334 of filter housing 324 is enlarged relative to proximal portion 332. In a preferred embodiment, distal portion 334 is adapted to receive at least a portion of filter 368. Filter 368 may be urged into a contracted configuration when it is partially or completely disposed within filter housing 324.

In the embodiment of FIG. 5, a guidewire 326 extends through distal guidewire port 376, guidewire lumen 350, and proximal guidewire port 374. Filter 368 is preferably fixed to the distal end of guidewire 326. In a preferred embodiment, distal portion 334 of filter housing 324 and tip member 336 are sized relative to one another so that tip member 336 will center guidewire 326 within filter housing 324.

Filter retrieval catheter 300 may be utilized to remove filter 368 from blood vessel 370. In a preferred embodiment, the physician may manipulate the distal portion of filter retrieval catheter 300 by applying forces to the proximal portion of filter retrieval catheter 300. In a particularly preferred embodiment, filter retrieval catheter 300 is adapted to provide hard stops that may be sensed by a physician using filter retrieval catheter 300 in a surgical procedure. These hard stops provide tactile feedback indicating that tip member 336 has been successfully placed in the desired position.

Figure 6:
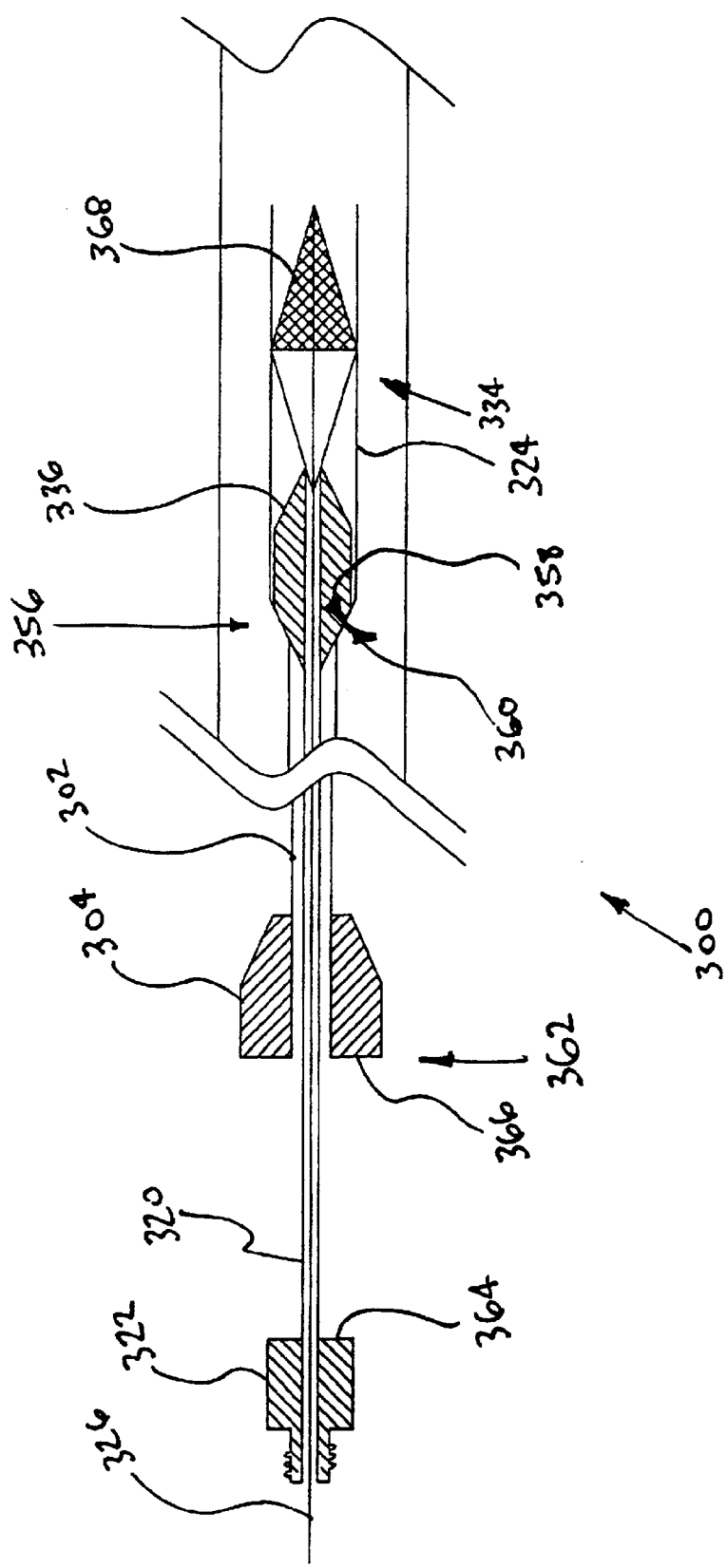
FIG. 6 is an additional partial cross-sectional view of filter retrieval catheter of FIG. 5.

FIG. 6 is an additional partial cross-sectional view of filter retrieval catheter 300 of FIG. 5. In the embodiment of FIG. 6, elongate shaft 302 and shaft hub 304 of filter retrieval catheter 300 have been moved relative to inner tubular member 320, ancillary hub 322, and guidewire 326. In the embodiment of FIG. 6, tip member 336 of filter retrieval catheter 300 is shown in a retracted position. In a preferred embodiment, filter housing 324 and tip member 336 are configured such that distal portion 334 of filter housing 324 may receive filter 368 when tip member 336 is in the retracted position shown. Tip member 336 of filter retrieval catheter 300 preferably also has an extended position as shown in FIG. 5

In FIG. 6, it may be appreciated that filter 368 has been urged into a contracted configuration. Filter retrieval catheter 300 preferably includes a proximal stop mechanism 356 that is adapted to stop relative movement between tip member 336 and filter housing 324 when tip member 336 is in the retracted position. In a particularly preferred embodiment, the relative movement required to move tip member 336 from the extended position to the retracted position is similar to the relative movement required to urge filter 368 into a contracted configuration within filter housing 324. Also in a particularly preferred embodiment, proximal stop mechanism 356 is adapted to provide a hard stop that may be sensed by a physician using filter retrieval catheter 300 in a surgical procedure. This hard stop provides tactile feedback indicating that tip member 336 has been successfully placed in the retracted position and filter 368 has been successfully urged into a contracted configuration.

In the embodiment of FIG. 6, proximal stop mechanism 356 includes a trailing surface 358 of tip member 336 and a mating surface 360 defined by a portion of filter housing 324. In the embodiment of FIG. 6, trailing surface 358 of tip member 336 seats against mating surface 360 when tip member 336 is in the retracted position.

Filter retrieval catheter 300 preferably also includes a distal stop mechanism 362 that is adapted to stop the movement of tip member 336 and inner tubular member 320 relative to filter housing 324 when tip member 336 is in the extended position. In the embodiment of FIG. 6, distal stop mechanism 362 includes a distal surface 364 of ancillary hub 322 and a proximal surface 366 of shaft hub 304. In the embodiment of FIG. 6, distal surface 364 of ancillary hub 322 may seat against proximal surface 366 of shaft hub 304 when tip member 336 is placed in the extended position.

In a preferred embodiment, tip member 336 and filter housing 324 are configured such that guidewire 326 is substantially centered within filter housing 324. Centering filter housing 324 about guidewire 326 may reduced the magnitude of force which is required to urge filter housing 324 over filter 368 and/or the magnitude of force which is required to urge filter 368 into a contracted configuration.

Having thus described the preferred embodiments of the present invention, those of skill in the art will readily appreciate that yet other embodiments may be made and used within the scope of the claims hereto attached. Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A catheter for retrieving a filter fixed to a guidewire disposed within a blood vessel, comprising:
    an elongate shaft;
    a housing fixed to the elongate shaft proximate a distal end thereof, the housing including a wire defining a cavity adapted to receive at least a portion of the filter therein;
    a tip member slidingly disposed within a cavity defined by the housing; and
    wherein the tip member is configured such that the guidewire is substantially centered within the housing.

2. The catheter of claim 1, further including an inner tubular member fixed to the tip member.

3. The catheter of claim 1, further including an inner tubular member fixed to the tip member; and
    wherein the inner tubular member extends through a shaft lumen defined by the elongate shaft.

4. The catheter of claim 1, wherein the tip member has an outer radial extent that is generally greater than an outer radial extent of the inner tubular member.

5. The catheter of claim 1, wherein the tip member has an outer diameter that is generally greater than an outer diameter of the inner tubular member.

6. The catheter of claim 1, wherein the tip member has an outer radial extent comprising an outer diameter; and
    the outer diameter of the tip member is slightly smaller than an inner diameter of the cavity defined by the housing.

7. The catheter of claim 2, wherein the catheter includes a guidewire lumen extending through the tip member and the inner tubular member.

8. The catheter of claim 2, wherein the catheter includes a guidewire lumen extending through the tip member and the inner tubular member; and
    the guidewire lumen has a guidewire lumen diameter that is similar to an outer diameter of the guidewire.

9. The catheter of claim 2, wherein the catheter includes a guidewire lumen extending through the tip member and the inner tubular member; and
    the guidewire lumen has a guidewire lumen diameter that is slightly larger than an outer diameter of the guidewire.

10. The catheter of claim 1, wherein the tip member includes a distal portion having a generally tapered shape.

11. The catheter of claim 1, wherein the housing comprises the wire forming a plurality of turns.

12. The catheter of claim 11, wherein adjacent turns of the wire contact each other across substantially their entire length.

13. The catheter of claim 11, wherein the wire turns are configured such that the housing has a high level of longitudinal pushability and a high level of a lateral flexibility.

14. A catheter for retrieving a filter fixed to a guidewire disposed within a blood vessel, comprising:

an elongate shaft having a proximal end, a distal end, and a lumen extending therethrough;

a housing fixed to the elongate shaft proximate the distal end thereof, the housing including a wire defining a cavity adapted to receive at least a portion of the filter therein;

a tip member slidingly disposed within a cavity defined by the housing;

the tip member having a first position and a second position; and wherein a tapered portion of the tip member extends distally from the housing when the tip member is in the first position.

15. The catheter of claim 14, wherein the housing and the tip member are configured such that the housing may accept the filter when the tip member is in the second position.

16. The catheter of claim 14, further including a first stop means for stopping the movement of the tip member and an inner tubular member when the tip member is in the first position.

17. The catheter of claim 16, further including:

a shaft hub disposed about the elongate shaft proximate a proximal distal end thereof;

an ancillary hub disposed about the inner tubular member proximate a proximal end thereof; and wherein the second stop means comprises a distal surface of the ancillary hub and a proximal surface of the shaft hub.

18. The catheter of claim 14, further including a second stop means for stopping the movement of the tip member and an inner tubular member when the tip member is in the second position.

19. The catheter of claim 18, wherein the second stop means comprises a trailing surface of the tip member and a mating surface of the housing.

20. The catheter of claim 14, further including an inner tubular member fixed to the tip member.

21. The catheter of claim 14, further including an inner tubular member fixed to the tip member; and wherein the inner tubular member extends through the lumen defined by the elongate shaft.

22. The catheter of claim 20, wherein the tip member has an outer radial extent that is generally greater than an outer radial extent of the inner tubular member.

23. The catheter of claim 20, wherein the tip member has an outer diameter that is generally greater than an outer diameter of the inner tubular member.

24. The catheter of claim 14, wherein the tip member has an outer radial extent comprising an outer diameter; and the outer diameter of the tip member is slightly smaller than an inner diameter of the cavity defined by the housing.

25. The catheter of claim 20, wherein the catheter includes a guidewire lumen extending through the tip member and the inner tubular member.

26. The catheter of claim 20, wherein the catheter includes a guidewire lumen extending through the tip member and the inner tubular member; and the guidewire lumen has a guidewire lumen diameter that is similar to an outer diameter of the guidewire.

27. The catheter of claim 20, wherein the catheter includes a guidewire lumen extending through the tip member and the inner tubular member; and the guidewire lumen has a guidewire lumen diameter that is slightly larger than an outer diameter of the guidewire.

28. The catheter of claim 14, wherein the housing comprises a wire forming a plurality of turns.

29. The catheter of claim 28, wherein adjacent turns of the wire contact each other across substantially their entire length.

30. The catheter of claim 28, wherein the wire turns are configured such that the housing has a high level of longitudinal pushability and a high level of lateral flexibility.

31. A catheter for retrieving a filter fixed to a guidewire disposed within a blood vessel, comprising:

an elongate shaft;

a housing fixed to the elongate shaft proximate a distal end thereof, wherein the housing comprises a wire forming a plurality of turns and defining a cavity adapted to receive at least a portion of the filter therein;

and a tip member slidably disposed within the cavity defined by the housing, and wherein the tip member is configured such that a guide wire is substantially centered within the housing.

32. The catheter in accordance with claim 31, further including an inner tubular member fixed to the tip member.

33. The catheter in accordance with claim 31, further including an inner tubular member fixed to the tip member wherein the inner tubular member extends through a shaft lumen defined by the elongate shaft.

34. The catheter in accordance with claim 31, wherein the tip member has an outer radial extent that is generally greater than an outer radial extent of an inner tubular member.

35. The catheter in accordance with claim 31, wherein the tip member has an outer diameter that is generally greater than the outer diameter of the inner tubular member.

36. The catheter in accordance with claim 31, wherein the tip member has an outer radial extent including an outer diameter, the outer diameter of the tip member being slightly smaller than the inner diameter of the cavity defined by the housing.

37. The catheter in accordance with claim 31, wherein the catheter includes a guidewire lumen extending through the tip member and an inner tubular member.

38. The catheter in accordance with claim 31, wherein the catheter includes a guidewire lumen extending through the tip member and an inner tubular member, the guidewire lumen having a guidewire lumen diameter that is similar to an outer diameter of the guidewire.

39. The catheter in accordance with claim 31, wherein the catheter includes a guidewire lumen extending to the tip member and an inner tubular member, the guidewire lumen having a guidewire lumen diameter that is slightly larger than an outer diameter of the guidewire.

40. The catheter in accordance with claim 31, wherein the tip member includes a distal portion having a generally tapered shape.

* * * * *